(12) United States Patent
Suddaby

(10) Patent No.: US 12,274,626 B2
(45) Date of Patent: Apr. 15, 2025

(54) FACET JOINT FIXATION DEVICE

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 0 days.

(21) Appl. No.: 17/807,435

(22) Filed: Jun. 17, 2022

(65) Prior Publication Data

US 2023/0404769 A1    Dec. 21, 2023

(51) Int. Cl.
*A61F 2/44* (2006.01)
*A61F 2/30* (2006.01)
*A61F 2/46* (2006.01)

(52) U.S. Cl.
CPC ........ *A61F 2/4405* (2013.01); *A61F 2/30771* (2013.01); *A61F 2/446* (2013.01); *A61F 2/4611* (2013.01); *A61F 2002/30845* (2013.01); *A61F 2002/4629* (2013.01)

(58) Field of Classification Search
CPC ............ A61B 17/7062; A61B 17/7064; A61F 2/4405
USPC .......................... 623/17.11–17.16
See application file for complete search history.

(56) References Cited

U.S. PATENT DOCUMENTS

| | | | |
|---|---|---|---|
| 6,436,141 B2 | 8/2002 | Castro et al. | |
| 7,608,105 B2 | 10/2009 | Pavlov et al. | |
| 7,819,905 B2 * | 10/2010 | Newcomb | A61B 17/8625 606/311 |
| 8,080,046 B2 | 12/2011 | Suddaby | |
| 8,162,981 B2 | 4/2012 | Vestgaarden | |
| 8,231,632 B1 * | 7/2012 | Jordan | A61B 17/8816 606/92 |
| 8,906,093 B2 | 12/2014 | Malone | |
| 9,717,603 B2 | 8/2017 | Davis | |
| 2009/0036927 A1 * | 2/2009 | Vestgaarden | A61B 17/7064 606/247 |
| 2012/0259365 A1 | 10/2012 | Richelsoph | |
| 2013/0226239 A1 * | 8/2013 | Altarac | A61B 17/864 606/279 |
| 2013/0253649 A1 * | 9/2013 | Davis | A61F 2/446 623/17.16 |
| 2014/0012381 A1 * | 1/2014 | Labrom | A61F 2/4405 623/17.16 |
| 2014/0058457 A1 * | 2/2014 | Appenzeller | A61B 17/864 606/305 |

(Continued)

FOREIGN PATENT DOCUMENTS

| | | |
|---|---|---|
| CN | 104970905 A | 10/2015 |
| CN | 213607208 U | 7/2021 |

*Primary Examiner* — Eduardo C Robert
*Assistant Examiner* — Christina Negrellirodriguez
(74) *Attorney, Agent, or Firm* — Harter Secrest & Emery LLP; Michael Nicholas Vranjes

(57) ABSTRACT

A joint fixation assembly for fusing bone, including a joint fixation device, including a first section including a first end, a second end, a first radially outward facing surface, and a first through-hole extending between the first end and the second end and forming a cavity, a second section arranged coaxially with the first section and including a third end fixedly secured to the second end, a fourth end, and a second radially outward facing surface including threading, and a second through-hole extending from the third end to the fourth end, and at least one projection extending radially outward first radially outward facing surface.

20 Claims, 8 Drawing Sheets

(56) References Cited

U.S. PATENT DOCUMENTS

2018/0303529 A1* 10/2018 Zastrozna .......... A61B 17/8635
2019/0388131 A1* 12/2019 Mehl ...................... A61B 17/86
2021/0346175 A1   11/2021 Glaser

* cited by examiner

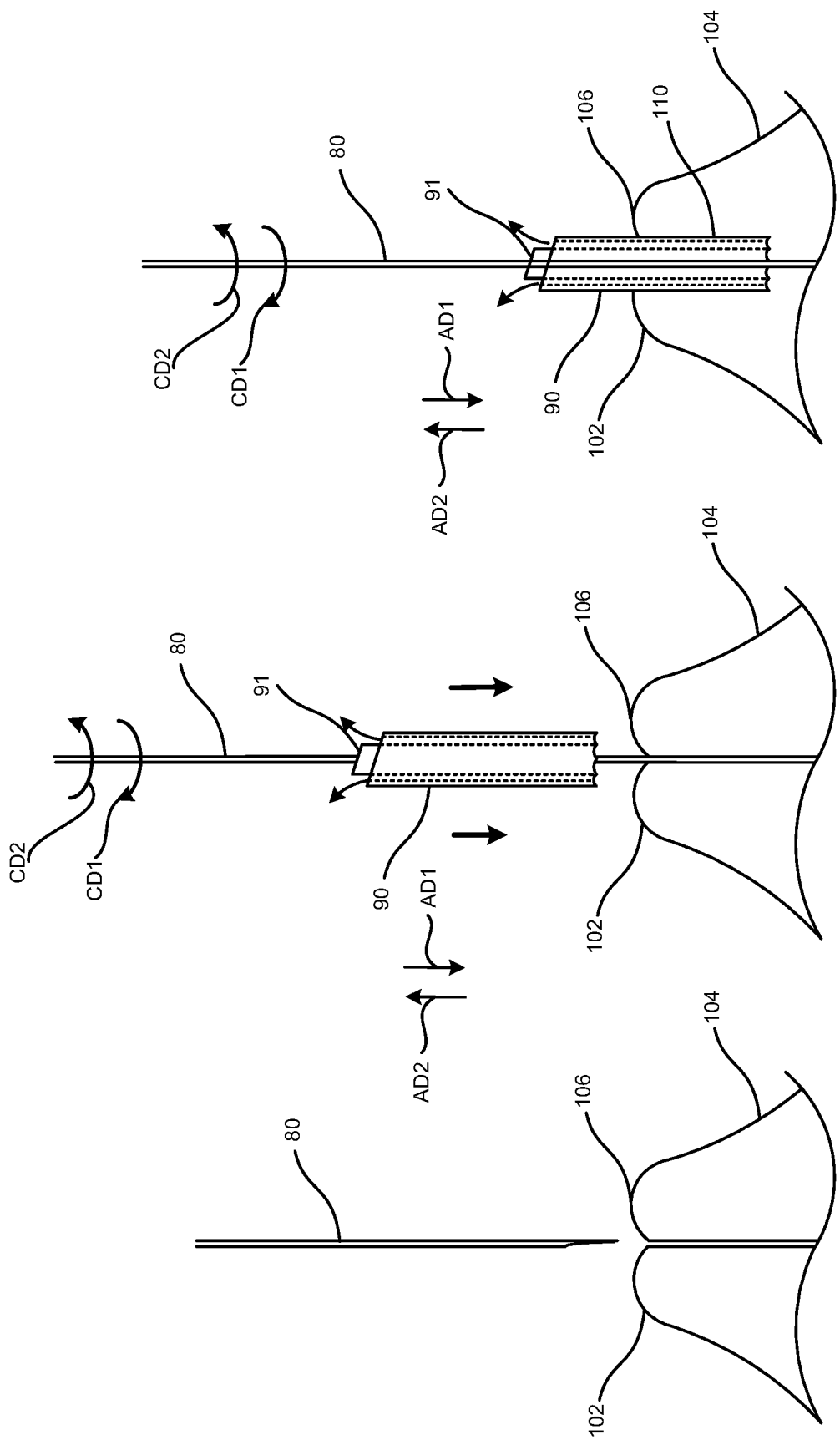

FACET JOINT FIXATION DEVICE

FIELD

The present disclosure relates to orthopedic surgery, and more particularly to interbone fixation and fusion devices, and even more particularly, to intraarticular facet joint fixation and fusion devices.

BACKGROUND

The intervertebral discs of the human spine are prone to degeneration. In particular, the intervertebral discs located in highly mobile regions of the spine are disproportionately prone to degeneration, primarily due to overt and covert trauma to the tissue that occurs in the course of repetitive activities. Such trauma tends to disrupt the internal architecture of the disc, and the eventual collapse of the disc space. The resultant mechanical and/or chemical irritation of the surrounding neural elements, such as the spinal cord and nerves, may cause pain, inflammation, and varying degrees of osteoarthritis and attendant disability. Additionally, the loss of disc space height relaxes tension on the longitudinal spinal ligaments, thereby contributing to varying degrees of spinal instability, further exacerbating the degenerative change.

Various treatments have been developed to treat such intervertebral disc degeneration. Many of these treatments involve the fusion of adjacent vertebra in order to limit their ability to move independently from each other, as such independent movement tends to exacerbate the degeneration of the interposed disc and associated facet joints. These prior spinal fusion operations often involve either the passive grafting of bone between the surfaces of proximate articular processes in a facet joint that is denuded of synovium, or they involve the mechanical fixation of the facet joint with a simple screw.

These prior treatments, while fairly adequate for their purpose, suffer from a number of drawbacks. For example, operations that involve the passive grafting of bone require additional instrumented fixation of the spine to prevent dislodgement of the bone grafts from between the articular surfaces of the joint. Simple screws are largely adjunctive, that is, the screw alone provides mechanical immobilization but without the addition of bone graft the screw is insufficient to guarantee fusion of the joint. The long term success of this procedure is usually dependent upon bony union occurring elsewhere between the adjacent vertebral elements being fused (i.e., interbody or intertransverse posterolateral fusions).

Thus, there is a long felt need for a facet fixation device that can be utilized either directly or in a stand-alone facet fusion procedure or as an adjunctive fixator to be utilized when other forms of spinal fusion are employed (i.e., as back up for an anterior fusion). There is also a long felt need for such a device that may be deployed radiographically or through endoscopically assisted minimally invasive approaches, and that such a device both stabilize the facet joint and facilitate fusion of the joint.

SUMMARY

According to aspects illustrated herein, there is provided a joint fixation assembly for fusing bone, comprising a joint fixation device, including a first section comprising a first end, a second end, a first radially outward facing surface, and a first through-hole extending between the first end and the second end and forming a cavity, a second section arranged coaxially with the first section and comprising a third end fixedly secured to the second end, a fourth end, and a second radially outward facing surface comprising threading, and a second through-hole extending from the third end to the fourth end, and at least one projection extending radially outward first radially outward facing surface.

In some embodiments, the at least one projection comprises a plurality of projections arranged linearly such that they form a line, the line being parallel with a central axis of the joint fixation device. In some embodiments, the plurality of projections comprises a first projection optimized to cut through bone in an axial direction, and a second projection. In some embodiments, the second projection is optimized to cut through bone in a circumferential direction. In some embodiments, the first projection comprises a first width and the second projection comprises a second width, the second width being less than the first width. In some embodiments, the plurality of projections further comprises a third projection.

In some embodiments, the at least one projection comprises a first plurality of projections arranged in a first line along the radially outward facing surface, and a second plurality of projections arranged in a second line along the radially outward facing surface, the first line and the second line being parallel with a central axis of the joint fixation device. In some embodiments, the first section comprises a first diameter and the second section comprises a second diameter, the first diameter being greater than the second diameter. In some embodiments, the first section further comprises at least one hole extending from the first radially outward facing surface to the cavity. In some embodiments, the second through-hole comprises a socket at the fourth end.

In some embodiments, the joint fixation assembly further comprises an insertion tool operatively arranged to be removably connected to the joint fixation device. In some embodiments, the insertion tool comprises a third through-hole including a threaded portion operatively arranged to threadedly engage with the threading. In some embodiments, the insertion tool comprises a width that is greater than the first diameter.

In some embodiments, the joint fixation assembly further comprises a cutting device, including a third radially outward facing surface, and at least one blade operatively arranged to cut through bone in an axial direction. In some embodiments, the at least one blade comprises a first width, the at least one projection comprises a second width, the second width being less than the first width.

According to aspects illustrated herein, there is provided a joint fixation assembly for fusing bone, comprising a joint fixation device, including a first section comprising a first end, a second end, a first radially outward facing surface, and a first through-hole extending between the first end and the second end and forming a cavity, a second section arranged coaxially with the first section and comprising a third end fixedly secured to the second end, a fourth end, and a second radially outward facing surface comprising an external threading, and a second through-hole extending from the third end to the fourth end, and at least one projection extending radially outward first radially outward facing surface, and an insertion tool including an internal threading operatively arranged to engage the external threading and removably connect the joint fixation device to the insertion tool.

In some embodiments, the at least one projection comprises a plurality of projections arranged linearly such that they form a line, the line being parallel with a central axis of the joint fixation device. In some embodiments, the plurality of projections comprises a first projection optimized to cut through bone, and a second projection. In some embodiments, the plurality of projections comprises a first projection comprising a first width, and a second projection comprising a second width, the second width being less than the first width.

According to aspects illustrated herein, there is provided a method of implanting a fixation device in a joint, comprising forming a hole in the joint, forming a groove along the inner surface of the hole in an axial direction, aligning a protrusion of the fixation device with the groove, inserting the fixation device into the hole in the axial direction, and displacing the fixation device in a circumferential direction until the protrusion is no longer aligned with the groove. In some embodiments, the groove is formed using a cutting tool. In some embodiments, the groove is formed using a chisel. In some embodiments, the groove is formed using projections arranged on the fixation device, the projections comprising functional shapes optimized for cutting (e.g., for axial cutting or for circumferential cutting).

According to aspects illustrated herein, there is provided a facet joint fixation device, an enlarged insertion tool, a plunger, and a cutting device. The facet joint fixation device is operatively arranged to be inserted into a hole in a facet joint, to fix adjacent vertebrae to each other (i.e., fusion). The facet joint fixation device comprises a proximal end including a threaded portion and a hole having some geometric shape for applying torque (e.g., Phillips head, torx head, hex head). Bone material may be packed into the facet joint fixation device, through the enlarged insertion tool, via the plunger. The threaded portion is arranged to threadably engage the threaded portion of the enlarged insertion tool for inserting the facet joint fixation device into the facet joint. The facet joint fixation device further comprises holes or windows that allow bone material packed in the device to fuse with adjacent vertebrae, thereby creating fusion across the facet joint. The facet joint fixation device further comprises radially outward extending projections. These projections are arranged to engage the adjacent vertebrae to prevent the facet joint fixation device from backing out. In some embodiments, the enlarged insertion tool should be larger (i.e., greater in diameter) than the facet fixation device and insertion hole to serve as a positive stop although it is recognized that other stop mechanisms may be employed allowing alternate shapes or diameters of the insertion device. The insertion device choice is by surgeon prerogative and may include an under sized insertion device whereby the device is inserted by Xray control or by surgeon judgment above. As such, the stop surface of the enlarged insertion tool will engage the surface of the vertebrae to prevent over insertion of the facet joint fixation device in the hole. Over insertion can cause significant damage and/or complications (i.e., implants are often over driven and hit nerves). The cutting device is generally cylindrical and the same diameter as the hole in the facet joint. The cutting device comprises radially outward extending projections/blades. The cutting device is arranged to be driven into the hole (e.g., using a hammer) to cut longitudinal grooves in the hole. The projections of the facet joint fixation device will engage these grooves.

To install/implant the device, first a hole is drilled into a facet joint. This can be done using a Kirschner wire or K-wire as a guide. Next, the cutting device is forced into the hole such that the blades produce longitudinal grooves down the sidewall of the hole. The cutting device is then removed. Next the facet joint fixation device is threadably engaged with the threaded portion of enlarged insertion tool. The projections of facet joint fixation device are aligned with the grooves of the hole, at which point the facet joint fixation device is inserted into the hole using the enlarged insertion tool until the stop surface of the tool engages the surface of the facet joint. Once fully inserted, using the tool, the facet joint fixation device is rotated (e.g., 10 degrees), which essentially moves the projections of the facet joint fixation device out of alignment with the grooves and prevents facet joint fixation device from being withdrawn from the hole. Using the plunger, bone material is then packed into the facet joint fixation device through the head. A tool or the plunger is then engaged with the head of the facet joint fixation device to prevent its rotation, at which point enlarged insertion tool is rotated to disengage it from the facet joint fixation device. The plunger/tool is then removed and the facet joint fixation device is left in the hole.

One key advantage of the device of the present disclosure is the protuberances or projections being arranged linearly so they can follow the cut grooves in the bone on insertion. This allows a more significant size to the protuberance upon insertion with less bone disruption than if they were arranged in a nonlinear fashion. The linear arrangement speaks to function that includes resistance to expulsion but requires linearity as well as a rotation of the device after implantation to gain the maximal effect of the protuberance as a hedge mitigating device dislodgement. In effect, this prevents dislodgement after placement. The arrangement of the present disclosure can be applied to any device place in bone, for example a bone anchor, and is not limited to just an interbody device or a joint fixation device. Contrarily, externally threaded devices like screws or smooth ones like nails are all prone to being expelled along their insertion path because of continued movement. In the device of the present disclosure, the tendency to expel is mitigated by the arrangement of external protuberances that engage the surface of the surrounding bone so as to frictionally and mechanically thwart migration. This being done by altering the rotational position of the device after implantation to position the protuberances in a different track than the one they were inserted along to maximize bone frictional contact.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIGS. 5A-G are side views showing steps in the implantation of a facet joint fixation device;

DETAILED DESCRIPTION

Figure 1:
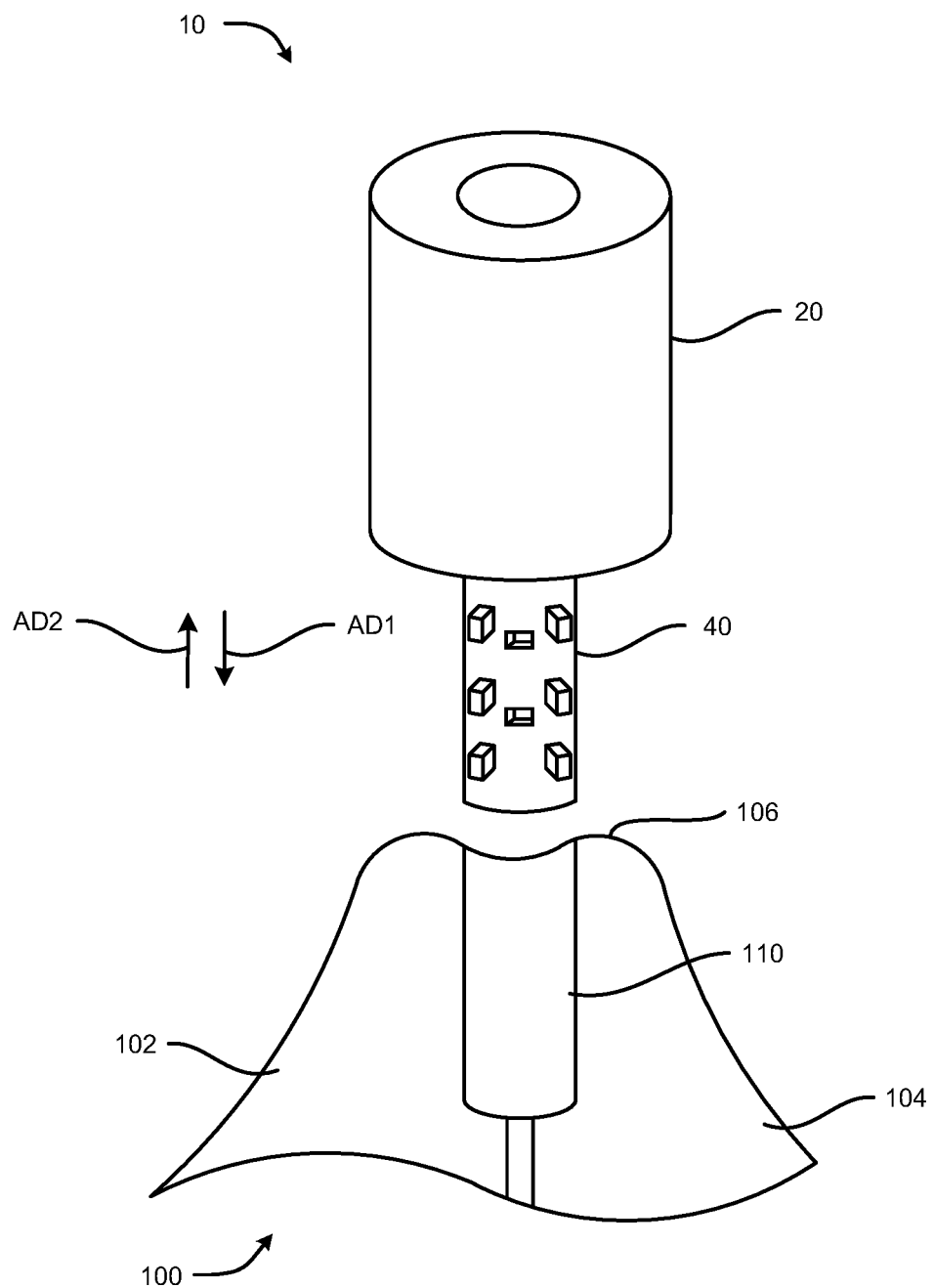
FIG. 1 is a perspective view of a joint fixation assembly arranged proximate to a joint.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein.

By "non-rotatably connected" elements, we mean that: the elements are connected so that whenever one of the elements rotate, all the elements rotate; and, relative rotation between the elements is not possible. Radial and/or axial movement of non-rotatably connected elements with respect to each other is possible, but not required. By "rotatably connected" elements, we mean that: the elements are rotatable with respect to each other; and, whenever one element is displaced radially and/or axially, all the elements are displaced radially and/or axially.

Figure 2:
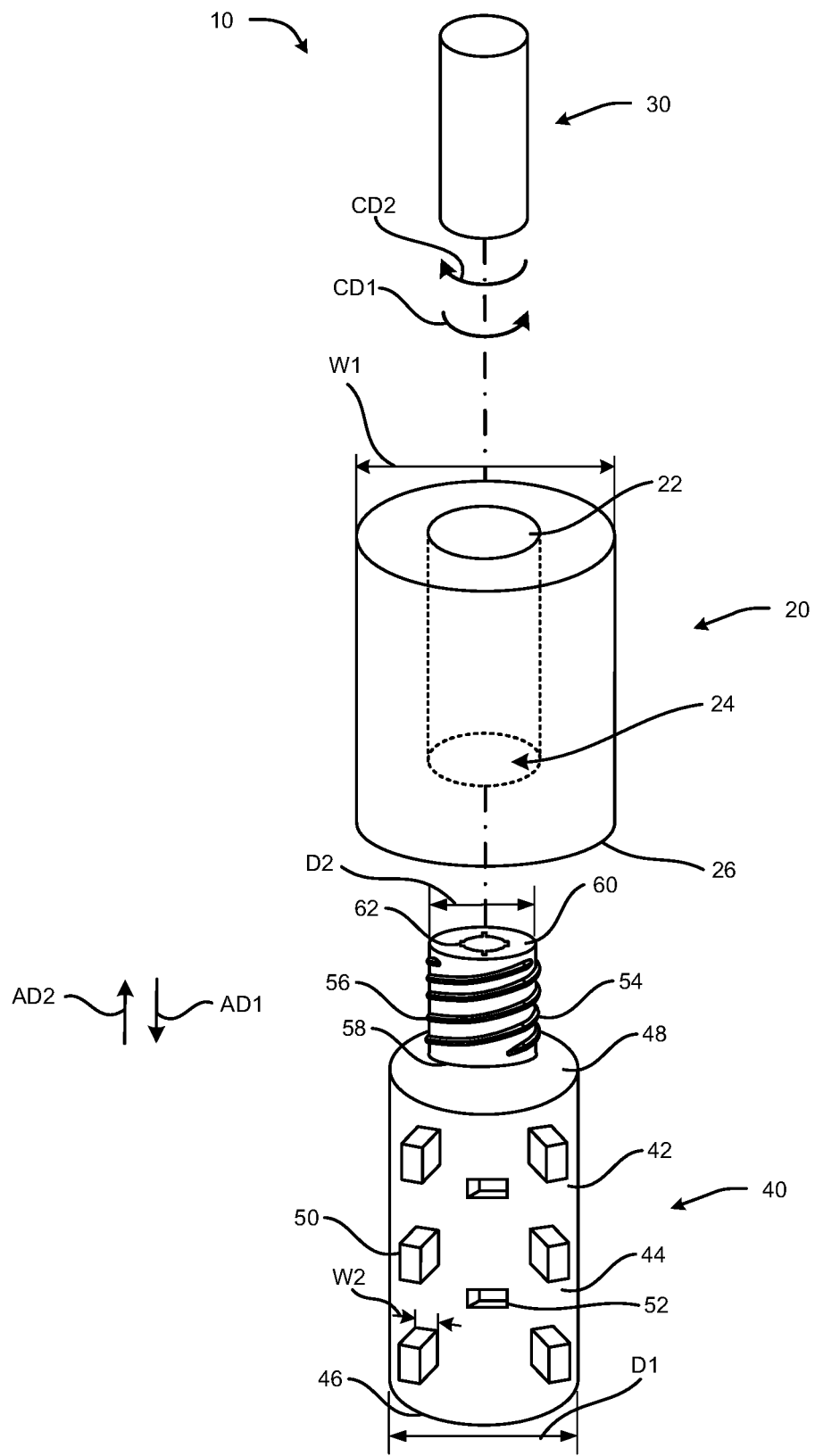
FIG. 2 is an exploded perspective view of a joint fixation assembly.

Adverting now to the figures, FIG. 1 is a perspective view of joint fixation assembly 10 arranged proximate to vertebra or joint or facet joint 100. FIG. 2 is an exploded perspective view of joint fixation assembly 10. Joint fixation assembly 10 generally comprises facet joint fixation device 40. In some embodiments, joint fixation assembly 10 further comprises insertion tool 20. In some embodiments, joint fixation assembly further comprises plunger 30. In some embodiments, joint fixation assembly further comprises cutting device 70.

Facet joint fixation device 40 comprises section 42 and section 54. Section 42 comprises radially outward facing surface 44, end 46, and end 48. In some embodiments section 42 is substantially cylindrical; however, it should be appreciated that section 42 may comprise any geometry suitable for insertion into cavity in bone, for example, square, rectangular prism, conical, frusto-conical, etc. Radially outward facing surface 44 comprises one or more projections 50. Projections 50 are operatively arranged to engage bone elements 102, 104 and prevent facet joint fixation device 40 from being dislodged from hole 110, as will be described in greater detail below. In some embodiments, and as shown, projections 50 are arranged linearly aligned along section 42. For example, section 42 may comprise four groups of projections 50, with each group of projections 50 being aligned along radially outward facing surface 44 in a linear line parallel to axial direction AD1, AD2. Such linear alignment of projections 50 allows facet joint fixation device 40 to be guided into hole 110 such that projections 50 align with axially formed grooves, as will be described in greater detail below. Moreover, the linear arrangement of projections allows for a more significant size to the projection upon insertion into hole 110 with less bone disruption than if they were in a nonlinear arrangement (i.e., bone disruption only occurs along the linear path). Section 42 further comprises one or more holes 52 extending from radially outward facing surface 44 to a center hole or through-hole of section 42. Holes 52 facilitate fusion and bone ingrowth into facet joint fixation device 40. Additionally, bone material packed into the inner hole of section 42 will fuse with bone elements 102, 104 through holes 52.

Section 54 is fixedly secured to section 42. Section 54 comprises radially outward facing surface 56, end 58, and end 60. In some embodiments, section 54 is substantially cylindrical and radially outward facing surface 56 comprises external threading. End 58 abuts against and is connected to end 48. Section 54 comprises hole 62 extending therethrough (i.e., from end 62 to end 58). Hole 62 provides a passage to the inner hole of section 42 through which bone material can be injected. Hole 62 comprises a head or socket at end 60 (e.g., Phillips head, torx head, hex head), such that a torque can be applied to facet joint fixation device, as will be described in greater detail below. In some embodiments, and as shown, section 42 comprises diameter D1 and section 54 comprises diameter D2, diameter D1 being greater than diameter D2. As such, radially outward facing surface 56 is arranged spaced radially inward from radially outward facing surface 44. In some embodiments, section 54 is arranged coaxial with section 42. In some embodiments, diameter D2 is equal to diameter D1.

Insertion tool 20 is operatively arranged to connect to facet joint fixation device 40 for insertion. Insertion tool 20 comprises hole 22 extending therethrough and surface 26. Hole 22 comprises threaded portion 24 arranged at or proximate to surface 26. Threaded portion 24 is operatively arranged to threadably engage threading 56 of section 54 to connect facet joint fixation device 40 to insertion tool 20. Specifically, section 54 is threaded into threaded portion 24 until send 48 abuts against surface 26, at which point insertion tool 20 and facet joint fixation device 40 are non-rotatably connected in a first circumferential direction CD1, CD2 (i.e., rotation of insertion tool 20 in the first circumferential direction results in rotation of facet joint fixation device 40 in the first circumferential direction). Rotation of insertion tool 20 in a second circumferential direction, opposite the first circumferential direction, does not always result in rotation of facet joint fixation device 40 in the second circumferential direction (i.e., the threading may disengage). Insertion tool 20 comprises width W1 that is greater than diameter D2 of section 42. This allows surface 26 to act as a stop and prevents over insertion of facet joint fixation device 40, as will be described in greater detail below.

Plunger 30 is generally a cylindrical tool that can be used to force bone material through insertion tool 20 via hole 22, section 54 via hole 62, and into the inner hole of section 42. In some embodiments, insertion tool 20 is connected to facet joint fixation device 40, specifically section 54. Facet joint fixation device 40 is inserted into joint 100, for example hole 110, until surface 26 abuts against surface 106. Then bone material is inserted into section 42. In some embodiments, bone material is inserted into section 42 prior to insertion of facet joint fixation device 40 into joint 100.

Figure 3:
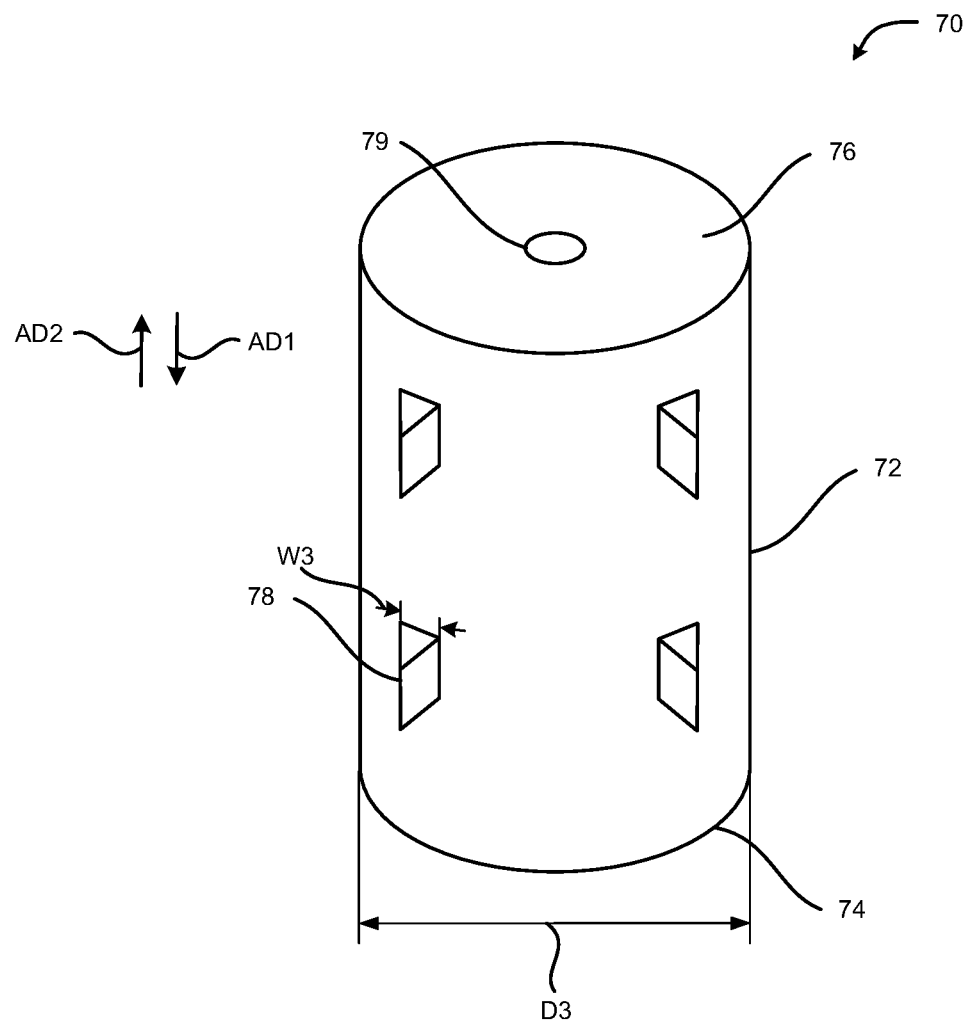
FIG. 3 is a perspective view of a cutting device.

FIG. 3 is a perspective view of cutting device 70. Cutting device 70 is operatively arranged to be inserted into hole 110 to form grooves longitudinally therein, for example, grooves 112 shown in FIGS. 6-7. Cutting device 70 comprises radially outward facing surface 72, end 74 and end 76. In some embodiments, cutting device 70 comprises through-hole 79 extending from end 76 to end 74. Through-hole 79 is operatively arranged to engage a K-wire, for example K-wire 80. Cutting device 70, and specifically radially outward facing surface 72, comprises diameter D3 which is substantially equal to diameter D1 and the diameter of hole 110, as will be described in greater detail below. Radially outward facing surface 72 comprises one or more blades 78 extending radially outward therefrom. Blades 78 are arranged such that, displacement of cutting device 70 in axial direction AD1 within hole 110 causes grooves to be formed. Put another way, blades 78 are arranged to cut through bone in axial direction AD1. As such, as cutting device 70 is forced into hole 110 in axial direction AD1, for example via a hammer, grooves 112 are formed in a longitudinal direction of hole 110. After cutting device 70 forms grooves 112 in hole 110, cutting device 70 can be removed. In some embodiments, cutting device 70 comprises one or more groups of blades 78, with each group of blades 78 being aligned along radially outward facing surface 72 in a linear line parallel to axial direction AD1, AD2. In some embodiments, blades 78 comprise width W3, which is substantially equal to width of groove 112. Projections 50 comprise width W2, which is less than or equal to width W3, thereby allowing for easy insertion of facet joint fixation device 40 into hole 110 once grooves 112 are formed.

Figure 4:
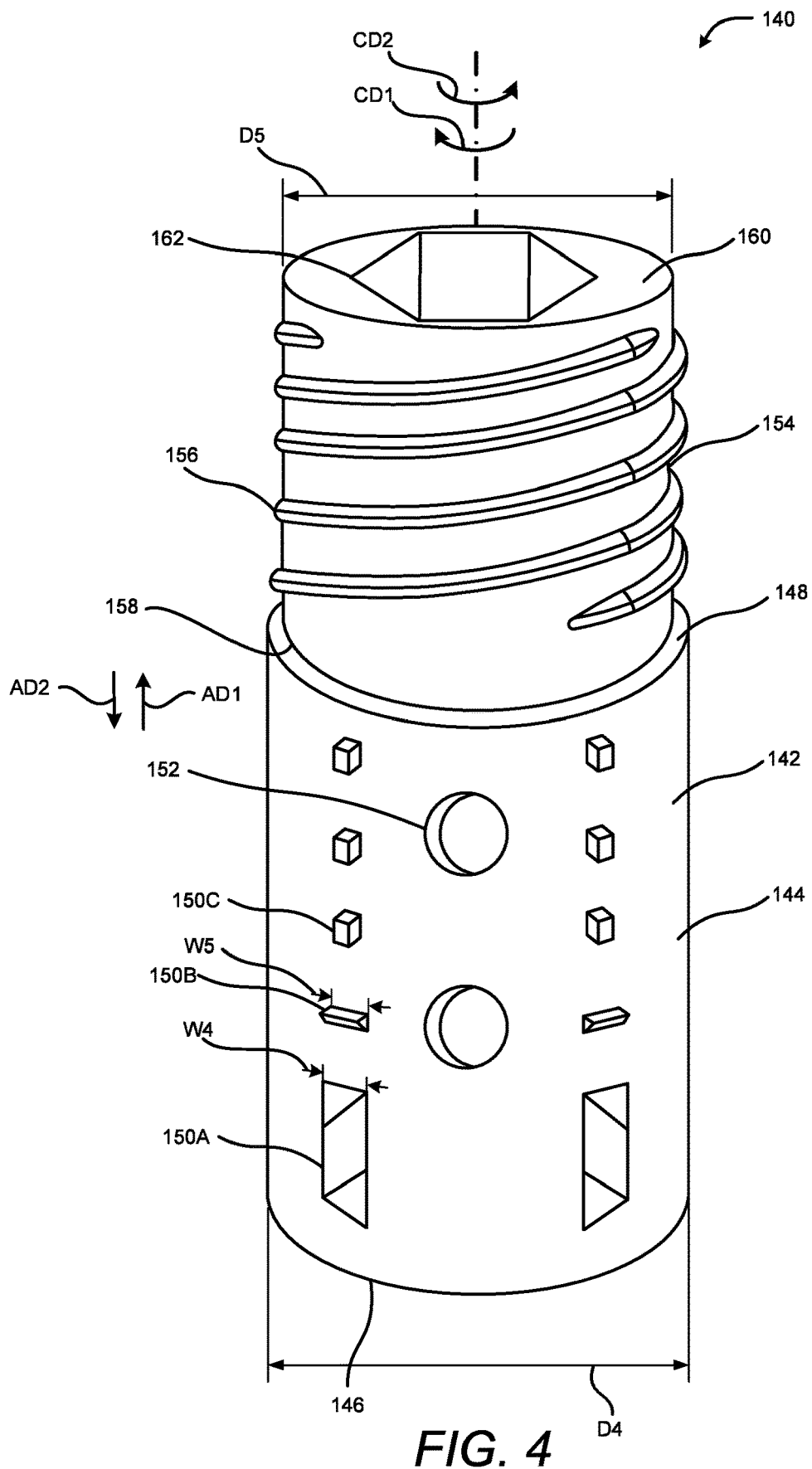
FIG. 4 is a perspective view of a facet joint fixation device.

FIG. 4 is a perspective view of facet joint fixation device 140. Facet joint fixation device 140 comprises section 142 and section 154. Section 142 comprises radially outward facing surface 144, end 146, and end 148. In some embodiments section 142 is substantially cylindrical; however, it should be appreciated that section 142 may comprise any geometry suitable for insertion into cavity in bone, for example, square, rectangular prism, conical, frusto-conical, etc. Radially outward facing surface 144 comprises one or more projections 150A, 150B, 150C, operatively arranged to engage bone elements 102, 104 and, inter alia, prevent facet joint fixation device 140 from being dislodged from hole 110, as will be described in greater detail below.

In some embodiments, the projections comprise groups of projections arranged in a linear line parallel to axial direction AD1, AD2. For example, a first group of projections may comprise projection or blade 150A, cutting projection or blade 150B, and one or more projections 150C linearly aligned along radially outward facing surface 144. Cutting projection 150A is optimized to cut grooves 112 in hole 110 in axial direction AD1. Specifically, blades 150A are arranged such that, displacement of facet joint fixation device 140 in axial direction AD1 within hole 110 causes grooves to be formed. Put another way, blades 150A are arranged to cut through bone in axial direction AD1. As such, as facet joint fixation device 140 is forced into hole 110 in axial direction AD1, for example via a hammer and/or insertion tool 20, grooves 112 are formed in a longitudinal direction of hole 110.

Cutting projection 150B is optimized to cut through bone in hole 110 in circumferential direction CD1 (or CD2). After facet joint fixation device 140 is fully inserted into hole 110 in axial direction AD1, facet joint fixation device 140 is displaced in circumferential direction CD1 or CD2. Cutting projection 150B facilitates this circumferential displacement and cuts a circumferential groove into the bone. It should be appreciated that the various projections need not necessarily comprise a blade facilitating cutting in circumferential direction CD1, CD2. For example, projection 150C will cut through bone elements 102 and 104 if/when enough force is applied to facet joint fixation device 140. Likewise, cutting projection 150A, although optimized for cutting action in axial direction AD1, will cut through bone elements 102 and 104 when facet joint fixation device 140 is displaced in circumferential direction CD1 and circumferential direction CD2 with enough force.

The linear arrangement of projections 150A, 150B, and 150C allows facet joint fixation device 140 to be efficiently and securely implanted. In some embodiments, cutting projection 150A comprises width W4 and cutting projection 150B comprises width W5, which is less than width W4. In some embodiments, projection 150C comprises a width that is less than width W4. Such arrangement allows for easier insertion of facet joint fixation device 140 into hole 110. Specifically, as facet joint fixation device 140 is inserted into hole 110 in axial direction AD1, cutting projection 150A cuts through bone element 102, 104 forming a groove therein. Since the width of cutting projection 150A is greater than the width of cutting projections 150B and 150C, cutting projections 150B and 150C do not engage bone elements 102 and 104 upon insertion of facet joint fixation device 140 into hole 110 in axial direction AD1.

As previously described, once fully inserted in hole 110, facet joint fixation device 140 is displaced circumferentially, for example, in circumferential direction CD1. Since one or more projections in a linear array on radially outward facing surface 144 comprises a circumferential cutting blade, for example, cutting projection 150B, facet joint fixation device 140 may be displaced circumferentially with greater ease. Put another way, the more projections with a circumferential cutting surface the easier it is to displace facet joint fixation device 140 circumferentially within hole 110. As such, in some embodiments projection 150B and projection 150B comprise circumferential cutting surfaces. In some embodiments, every projection in a linear array of projections comprises a circumferential cutting surface except for axial cutting projection 150A.

It should be appreciated that circumferential cutting projection as used herein is intended to mean a projection that is optimized for cutting in first circumferential direction CD1 or circumferential direction CD2, for example, circumferential cutting projection 150B. In some embodiments circumferential cutting projections comprise a cutting surface for cutting in only one circumferential direction CD1 and not the opposite circumferential direction CD2, and those circumferential cutting projections resist displacement in circumferential direction CD2. This arrangement is desirable as it facilitates displacement of facet joint fixation device 140 in a first circumferential direction and inhibits displacement of facet joint fixation device 140 in the second circumferential direction (i.e., prevents dislodgement and/or backing out of facet joint fixation device 140 from hole 110).

It should be appreciated that axial cutting projection as used herein is intended to mean a projection that is optimized for cutting in axial direction AD1, for example, axial cutting projection 150A. In some embodiments axial cutting projections comprise a cutting surface for cutting in only one axial direction AD1 and not the opposite axial direction AD2, and those axial cutting projections resist displacement in axial direction AD2. This arrangement is desirable as it facilitates displacement of facet joint fixation device 140 in a first axial direction and inhibits displacement of facet joint fixation device 140 in the second axial direction (i.e., prevents dislodgement and/or backing out of facet joint fixation device 140 from hole 110).

Section 142 further comprises one or more holes 152 extending from radially outward facing surface 144 to a center hole or through-hole of section 142. Holes 152 facilitate fusion and bone ingrowth into facet joint fixation device 140. Additionally, bone material packed into the inner hole of section 142 will fuse with bone elements 102, 104 through holes 152.

Section 154 is fixedly secured to section 142. Section 154 comprises radially outward facing surface 156, end 158, and end 160. In some embodiments, section 154 is substantially cylindrical and radially outward facing surface 156 comprises external threading. End 158 abuts against and is connected to end 148. Section 154 comprises hole 162 extending therethrough (i.e., from end 162 to end 158). Hole 162 provides a passage to the inner hole of section 142 through which bone material can be injected. Hole 162 comprises a head or socket at end 160 (e.g., Phillips head, torx head, hex head), such that a torque can be applied to facet joint fixation device, as will be described in greater detail below. In some embodiments, and as shown, section 142 comprises diameter D4 and section 154 comprises diameter D5, diameter D4 being greater than diameter D5.

As such, radially outward facing surface 156 is arranged spaced radially inward from radially outward facing surface 144. In some embodiments, section 154 is arranged coaxial with section 142. In some embodiments, diameter D5 is equal to diameter D4.

Figure 5E:
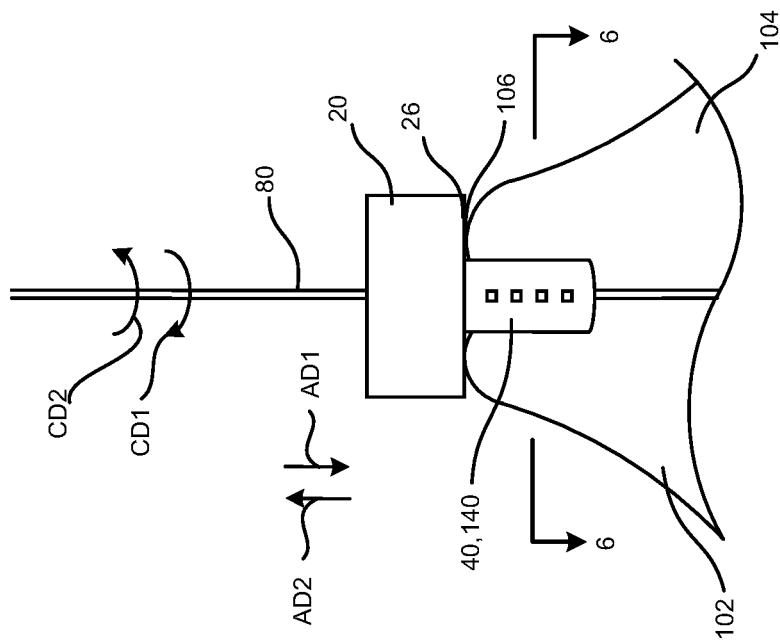

FIGS. 5A-G illustrate a method or procedure by which device 40, 140 is implemented. Particularly, FIGS. 5A-C illustrate a method by which proximate bone elements 102 and 104 are suitably prepared for implementation of device 40, 140, and FIGS. 5D-G illustrate the method by which device 40, 140 is implanted between the suitably prepare proximate bone elements 102 and 104.

As shown in FIG. 5A, the initial step in the procedure includes inserting K-wire between proximate bone elements 102 and 104 (i.e., joint or facet joint 100). K-wire 80 is operatively arranged to guide the tools involved in suitably preparing proximate bone elements 102 and 104, as well as, the various components of assembly 10, toward proximate bone elements 102 and 104.

FIG. 5B illustrates the second step in the procedure wherein drill 90 is guided by K-wire 80 toward bone elements 102 and 104, as indicated by the arrows. Drill 90 is preferably hollow so that K-wire 80 can be arranged in its interior, in order to guide it toward proximate bone elements 102 and 104. Additionally, first drill 90 may include suction channel 91, which is operatively arranged to remove excess bone material created by the drilling process, as is illustrated by the arrows proximate to channel 91 in FIGS. 5B-C. This excess bone material can later be used as fusion material (i.e., packed back into device 40, 140 once fully implanted).

FIG. 5C illustrates the third step in the procedure wherein drill 90 removes bone material from both proximate bone elements 102 and 104.

Figure 5D:
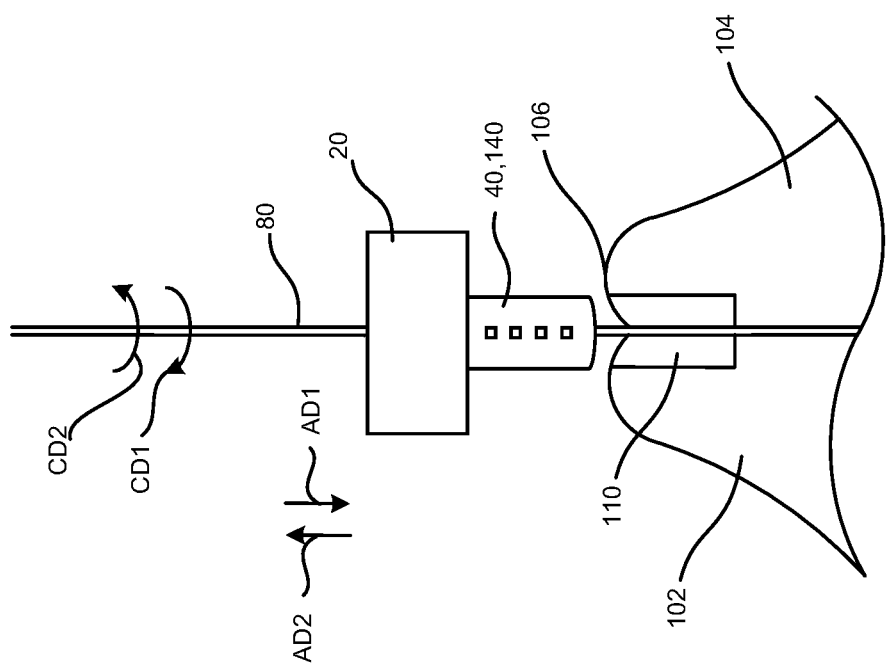

As shown in FIG. 5D, drill 90 is operatively arranged to remove bone material from bone elements 102 and 104, thereby generating cavity or hole 110, which is defined by bone elements 102 and 104. Hole 110 is arranged to receive inter-bone implant 40, 140 therein. Figure illustrates the fourth step in the procedure wherein joint fixation assembly 10 is guided by K-wire 80 toward hole 110. As shown, implant 40, 140 is threadedly connected to insertion tool 20, both being guided along K-wire 80 via respective holes (e.g., inner hole of section 42, 142, hole 62, 162, and hole 22.

FIG. 5E illustrates the fifth step in the procedure wherein device 40, 140 is arranged between suitably prepared bone elements 102 and 104. Device 40, 140 is preferably arranged such that radially outward facing surface 44, 144 is in contact with proximate bone elements 102 and 104. More particularly, protrusions 50, 150A-C are engaged with grooves 112. For device 140, grooves 112 are formed by cutting projections 150A as device 140 is inserted in hole 110 in axial direction AD1.

Figure 6:
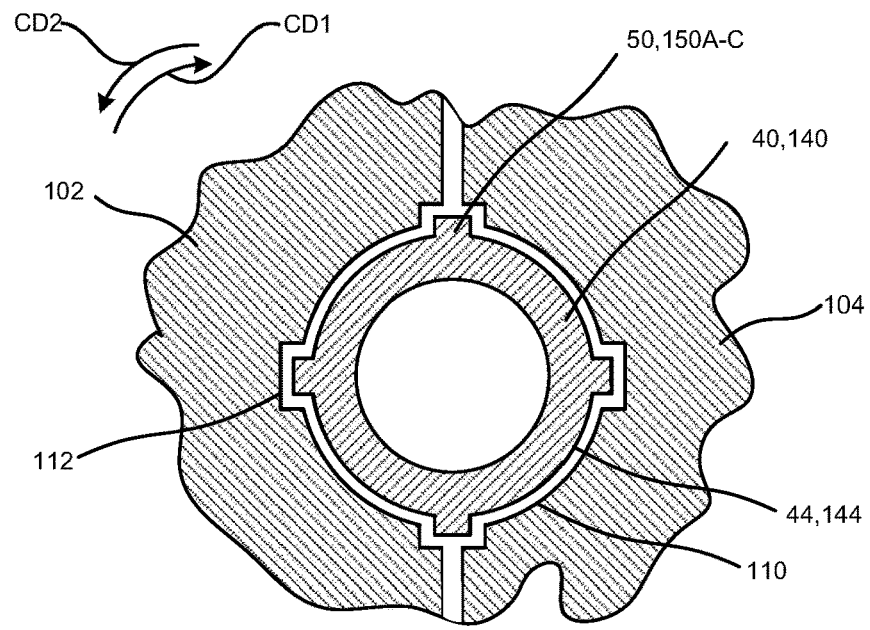
FIG. 6 is a cross-sectional view of the facet joint fixation device taken generally along line 6-6 in FIG. 5E; and, FIG. 7 is a cross-sectional view of the facet joint fixation device taken generally along line 7-7 in FIG. 5F.

For device 40, grooves 112 may also be formed by projections 50 as device 40 is inserted in hole 110 in axial direction AD1. However, for device 40 it is desirable to, in an additional step prior to insertion of device 40, to form grooves 112 using cutting device 70. Thus, cutting device 70 is guided along K-wire 80 via hole 79. Blades 78 form grooves 112 as device 40 is displaced in hole 110 in axial direction AD1. Cutting device 70 is then removed from hole 110. Subsequently, device 40 is inserted into hole 110 with the linear array of projections 50 aligned with grooves 112, as shown in FIG. 5E. FIG. 6 is a cross-sectional view of facet joint fixation device 40, 140 taken generally along line 6-6 in FIG. 5E. As shown, the linear array of projections 50, 50A-C are aligned and arranged within grooves 112. Radially outward facing surface 44, 144 is arranged proximate to or engages or abuts against the radially inward facing surface of hole 110.

As shown in FIG. 5E, device 40, 140 is fully inserted when surface 26 of insertion tool 20 engages and/or abuts against surface 106, which is an outermost surface of joint 100. The engagement of surface 26 with surface 106 prevents over insertion of device 40, 140 in hole 110 and/or joint 100, which can lead to significant problems (e.g., hitting a nerve). Once fully inserted, insertion tool 20, and thus device 40, 140 is displaced in a first circumferential direction, for example, circumferential direction CD1.

Figure 5F:
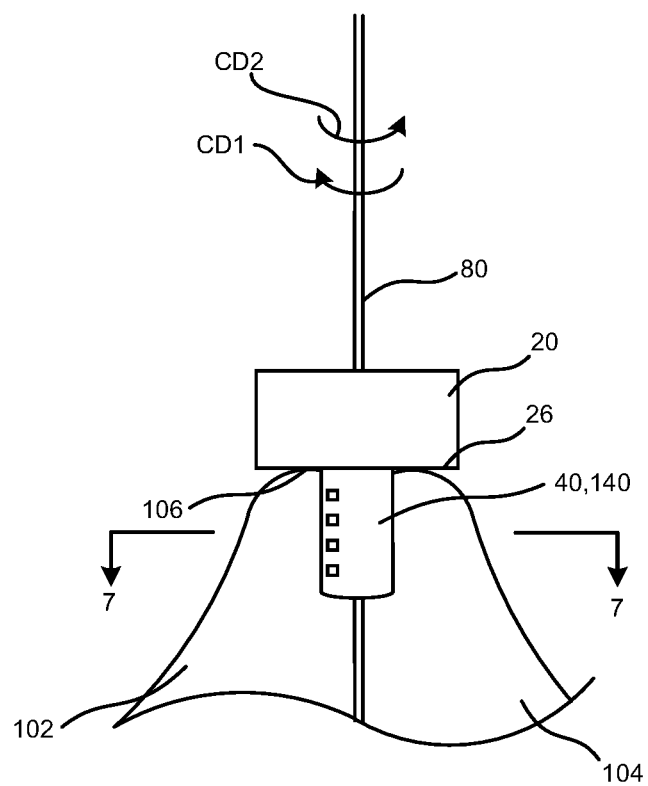
Figure 7:
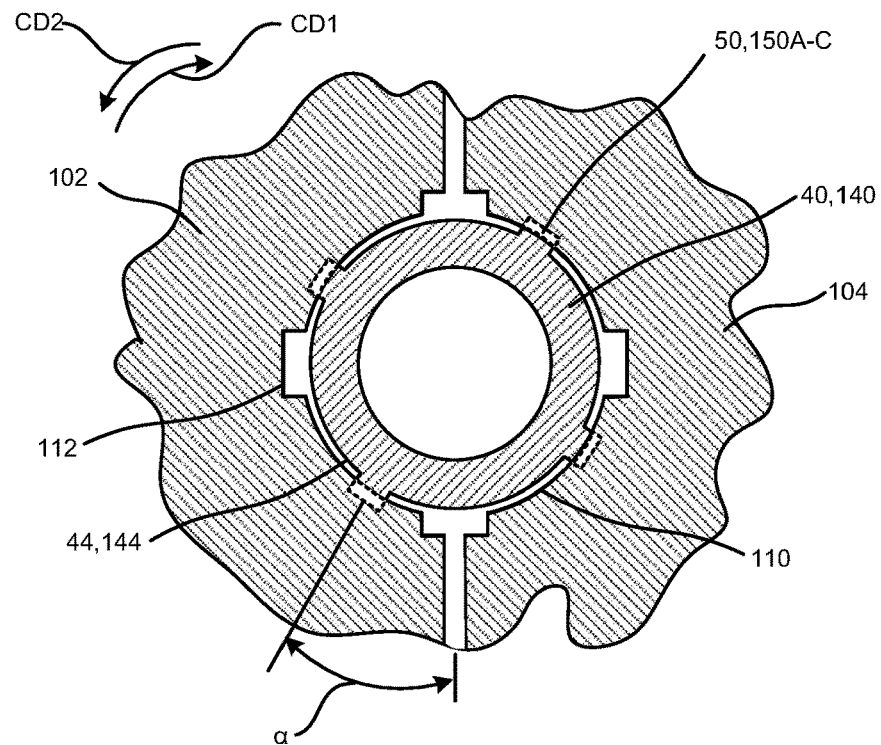

As shown in FIG. 5F, device 40, 140 has been displaced in circumferential direction CD1. FIG. 7 is a cross-sectional view of device 40, 140 taken generally along line 7-7 in FIG. 5F. As shown, device 40, 140 has been displaced by angle α in circumferential direction CD1 such that projections 50, 150A-C are no longer aligned with grooves 112. In this position, device 40, 140 cannot be removed from hole 110 in axial direction AD2. Next, bone material can be packed into device 40, 140. As previously described, bone material is forced through hole 22 of insertion tool 20 and hole 62, 162 of section 54, 154, and into the central cavity of 42, 142, for example, using plunger 30. The previously harvested bone (i.e., the bone that was removed by drill 90) may be used as the bone filling material; however, it should be appreciated that any other suitable bone material can be used, for example, autograft, allograft, and xenograft bone tissue, alloplast (hydroxyapatite, tricalcium phosphate (TCP), bioglass, etc.), and bone material, growth factors.

Figure 5G:
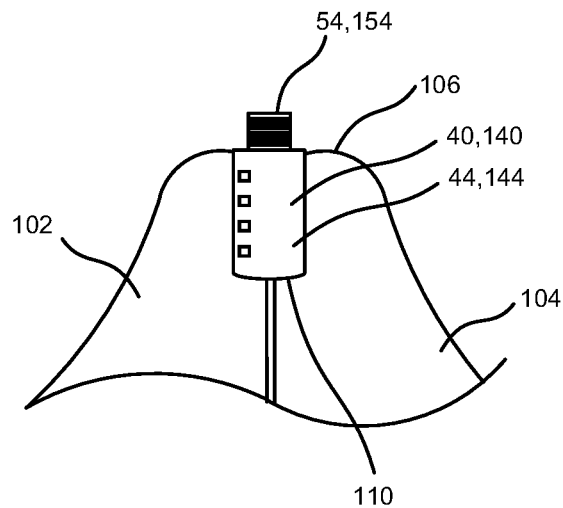

After device 40, 140, and specifically section 42, 142, is sufficiently filled with bone material, a tool having a head corresponding to the geometric shape of hole 62, 162 is passed through hole 22 to engage section 54, 154. Once engaged, insertion tool 20 is rotated out of engagement with section 54, 154 (i.e., the tool prevents rotation of device 40, 140) and removed from device 40, 140. K-wire 80 can then be removed. As shown in FIG. 5G, device 40, 140 is left in situ within join 100. Over time, fusion will occur, through device 40, 140, between bone element 102 and bone element 104. In some embodiments, section 54, 154 may be removed from section 42, 142.

It should be appreciated that while the present disclosure illustrates the fixation device being arranged in a joint such as a facet joint, device 40, 140 can be used in any joint or bone for which fusion is desired.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Bone or joint or facet joint fixation assembly
20 Insertion tool
22 Hole
24 Threaded portion
26 Surface
30 Plunger
40 Facet joint fixation device
42 Section
44 Radially outward facing surface
46 End
48 End
50 Projections
52 Hole(s)
54 Section
56 Radially outward facing surface or threading
58 End
60 End
62 Hole
70 Cutting device
72 Radially outward facing surface
74 End
76 End
78 Cutting projections(s) or blade(s)
79 Hole
80 K-wire
90 Drill
91 Channel
100 Vertebra or joint or facet joint
102 Bone element
104 Bone element
106 Surface
110 Hole
112 Grooves
140 Facet joint fixation device
142 Section
144 Radially outward facing surface
146 End
148 End
150A Cutting projection(s) or blade(s)
150B Cutting projection(s) or blade(s)
150C Projection(s)
152 Hole(s)
154 Section
156 Radially outward facing surface or threading
158 End
160 End
162 Hole
AD1 Axial direction
AD2 Axial direction
CD1 Circumferential direction
CD2 Circumferential direction
D1 Diameter
D2 Diameter
W1 Width
W2 Width
W3 Width
W4 Width
W5 Width
α Angle

What is claimed is:
1. A joint fixation assembly for fusing bone, comprising:
a joint fixation device, including:
  a first section comprising:
    a first end;
    a second end;
    a first radially outward facing surface; and
    a first through-hole extending between the first end and the second end and forming a cavity;
  a second section arranged coaxially with the first section and comprising:
    a third end fixedly secured to the second end;
    a fourth end;
    a second radially outward facing surface comprising threading; and
    a second through-hole extending from the third end to the fourth end;

a first projection extending radially outward from the first radially outward facing surface, the first projection being noncontinuous in a circumferential direction and optimized to cut through bone in an axial direction; and
a second projection.

2. The joint fixation assembly as recited in claim 1, wherein the first projection and the second projection are arranged linearly such that they form a line, the line being parallel with a central axis of the joint fixation device.

3. The joint fixation assembly as recited in claim 1, wherein the second projection is optimized to cut through bone in a circumferential direction.

4. The joint fixation assembly as recited in claim 1, wherein the first projection comprises a first width in a circumferential direction and the second projection comprises a second width in a circumferential direction, the second width being less than the first width.

5. The joint fixation assembly as recited in claim 4, further comprising a third projection.

6. The joint fixation assembly as recited in claim 1, wherein the joint fixation device comprises:
a first plurality of projections arranged in a first line along the first radially outward facing surface; and
a second plurality of projections arranged in a second line along the first radially outward facing surface, the first line and the second line being parallel with a central axis of the joint fixation device.

7. The joint fixation assembly as recited in claim 1, wherein the first radially outward facing surface comprises a first diameter and the second radially outward facing surface comprises a second diameter, the first diameter being greater than the second diameter.

8. The joint fixation assembly as recited in claim 1, wherein the first section further comprises at least one hole extending from the first radially outward facing surface to the cavity.

9. The joint fixation assembly as recited in claim 1, wherein the second through-hole comprises a socket at the fourth end.

10. The joint fixation assembly as recited in claim 1, further comprising an insertion tool operatively arranged to be removably connected to the joint fixation device.

11. The joint fixation assembly as recited in claim 10, wherein the insertion tool comprises a third through-hole including a threaded portion operatively arranged to threadedly engage with the threading.

12. The joint fixation assembly as recited in claim 10, wherein the insertion tool comprises a width that is greater than a first diameter of the first section.

13. The joint fixation assembly as recited in claim 1, further comprising
a cutting device, including:
a third radially outward facing surface; and
at least one blade extending radially outward from the third radially outward facing surface and operatively arranged to cut through bone in an axial direction.

14. The joint fixation assembly as recited in claim 13, wherein the at least one blade comprises a first width in a circumferential direction, the second projection comprises a second width in a circumferential direction, the second width being less than the first width.

15. A joint fixation assembly for fusing bone, comprising:
a joint fixation device, including:
a first section comprising:
a first end;
a second end;
a first radially outward facing surface; and
a first through-hole extending between the first end and the second end and forming a cavity;
a second section arranged coaxially with the first section and comprising:
a third end fixedly secured to the second end;
a fourth end;
a second radially outward facing surface comprising an external threading; and
a second through-hole extending from the third end to the fourth end; and
at least one projection extending radially outward from the first radially outward facing surface, the at least one projection being noncontinuous in a circumferential direction; and
an insertion tool including:
an internal threading operatively arranged to engage the external threading and removably connect the joint fixation device to the insertion tool; and
a third through-hole aligned with the second-through hole and the first through-hole, the third through-hole operatively arranged to allow bone material to be injected through the insertion tool and into the joint fixation device.

16. The joint fixation assembly as recited in claim 15, wherein the at least one projection comprises a plurality of projections arranged linearly such that they form a line, the line being parallel with a central axis of the joint fixation device.

17. The joint fixation assembly as recited in claim 16, wherein the plurality of projections comprises:
a first projection optimized to cut through bone in an axial direction; and
a second projection.

18. The joint fixation assembly as recited in claim 16, wherein the plurality of projections comprises:
a first projection comprising a first width; and
a second projection comprising a second width, the second width being less than the first width.

19. The joint fixation assembly as recited in claim 15, wherein the insertion tool further comprises a surface operatively arranged to prevent over insertion of the joint fixation device.

20. A method of implanting a fixation device in a joint, comprising:
forming a hole in the joint;
forming a linear groove along an inner surface of the hole in an axial direction;
aligning a protrusion of the fixation device with the groove;
inserting the fixation device into the hole in the axial direction; and
displacing the fixation device in a circumferential direction until the protrusion is no longer aligned with the groove.

* * * * *